United States Patent [19]
Lin et al.

[11] Patent Number: 5,936,108
[45] Date of Patent: Aug. 10, 1999

[54] METALLOCENE SYNTHESIS

[75] Inventors: Ronny W. Lin; Bruce C. Berris; John M. Power; Troy E. DeSoto; John F. Balhoff; Jamie R. Strickler, all of Baton Rouge, La.

[73] Assignee: Albemarle Corporation, Richmond, Va.

[21] Appl. No.: 08/998,105

[22] Filed: Dec. 24, 1997

Related U.S. Application Data

[63] Continuation-in-part of application No. 08/730,801, Oct. 17, 1996, abandoned.
[51] Int. Cl.$^6$ .................... C07F 17/00; C07F 7/00
[52] U.S. Cl. .................. 556/11; 556/53; 556/56; 526/160; 526/943; 502/103; 502/117
[58] Field of Search ................ 556/11, 53, 56; 526/160, 943; 502/103, 117

[56] References Cited

U.S. PATENT DOCUMENTS

| | | | |
|---|---|---|---|
| 4,528,408 | 7/1985 | Plummer | 568/808 |
| 4,794,096 | 12/1988 | Ewen | 502/117 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,036,034 | 7/1991 | Ewen | 502/117 |
| 5,120,867 | 6/1992 | Welborn, Jr. | 556/12 |
| 5,145,819 | 9/1992 | Winter et al. | 502/117 |
| 5,296,434 | 3/1994 | Karl et al. | 502/117 |
| 5,314,973 | 5/1994 | Welborn, Jr. | 526/126 |
| 5,324,800 | 6/1994 | Welborn, Jr. et al. | 526/160 |
| 5,329,033 | 7/1994 | Spaleck et al. | 556/53 |
| 5,441,920 | 8/1995 | Welborn, Jr. | 502/103 |
| 5,455,365 | 10/1995 | Winter et al. | 556/7 |
| 5,455,366 | 10/1995 | Rohrmann et al. | 556/8 |
| 5,512,693 | 4/1996 | Rosen et al. | 556/7 |
| 5,532,396 | 7/1996 | Winter et al. | 556/11 |
| 5,541,350 | 7/1996 | Murata et al. | 556/10 |
| 5,556,997 | 9/1996 | Strickler et al. | 556/11 |
| 5,569,746 | 10/1996 | Lee et al. | 534/11 |
| 5,585,508 | 12/1996 | Kuber et al. | 556/11 |

FOREIGN PATENT DOCUMENTS

| | | |
|---|---|---|
| 2055218 | 5/1992 | Canada . |
| 2084016 | 5/1993 | Canada . |
| 0530908 | 3/1993 | European Pat. Off. . |
| 0581754 | 2/1994 | European Pat. Off. . |
| 4434640 | 2/1996 | Germany . |
| 646438 | 11/1984 | Switzerland . |

OTHER PUBLICATIONS

Fierro et al., Journal of Organometallic chemistry, vol. 485, pp. 11–17, 1995.

Ray and Westland; "The Infrared Spectra of Some Compounds of Zirconium(IV) and Hafnium(IV) Tetrahalides and Ligands Containing Group V Donor Atoms"; Inorganic Chemistry, vol. 4, No. 10, Oct. 1965, pp. 1501–1504.

Spaleck, et al., The Influence of Aromatic Substituents on the Polymerization Behavior of Bridged Zirconocene Catalysts; Organometallics, vol. 3, 1994, pp. 954–963.

Spaleck, et al., "High Molecular Weight Polypropylene through Specifically Designed Zirconocene Catalysts"; Angew Chem. Int. Ed. Engl, 1992, vol. 31, No. 10, pp. 1347–1350.

Jordan, et al., "Synthesis and Structures of Neutral and Cationic rac–(Ethylenebis(tetrahydroindenyl))zirconium(IV) Benzyl Complexes"; Organometallics, vol. 9, No. 5, 1990, pp. 1539–1545.

Samuel et al; "$\pi$–Cyclopentadienyl and $\pi$–Indenyl Compounds of Titanium, Zirconium, and Hafnium Containing $\alpha$–Bonded Organic Substituents"; Journal of the American Chemical Society, 1973, 95:19; pp. 6263–6267.

The Metallocene Monitor, Special Feature; Exxon, Hoechst, and BASF All Have Parts of Metallogene–Catalyzed Isotactic PP; pp. 4–10; (undated).

Manriquez et al., "Reduction of Carbon Monoxide Promoted by Alkyl and Hydride Derivatives of Permethyzirconocene", Journal of the American Chemical Society, vol. 100, 1978, pp. 2716–2724.

Stehling, et al., "ansa–Zirconocene Polymerization Catalysts with Annelated Ring Ligands–Effects on Catalytic Activity and Polymer Chain Length"; Organometallics, 1994, vol. 13, No. 3, pp. 964–970.

Miller et al., "Activation of Benzene Carbon–Hydrogen Bonds via Photolysis or Thermolysis of ($\int \eta^5$–$C_5Me_5$)$_2$Zr(alkyl)H. Isolation of . . . ", Organometallics, 1988, vol. 7, pp. 818–825.

Primary Examiner—Porfirio Nazario-Gonzalez
Attorney, Agent, or Firm—Philip M. Pippenger

[57] ABSTRACT

A metallocene having one or two hydrocarbyl groups bonded to a Group 4 metal are produced from a crude impure pasty or non-wet mixture containing at least 50% by weight of a metallocene having two halogen atoms bonded to a Group 4 metal atom, by (a) mixing liquid aromatic hydrocarbon with the crude impure pasty or non-wet mixture; (b) mixing a solution of an organolithium compound in a suitable anhydrous ether or paraffinic hydrocarbon solvent or a mixture thereof, with the mixture from (a) and agitating the resulting mixture so that lithium halide solids are formed; and (c) separating the solids and recovering the resultant liquid portion which is mainly a solution of the metallocene having one or two hydrocarbyl groups bonded to a Group 4 metal. Additional optional steps include (d) replacing the original solvent from the solution from (c) with a liquid paraffinic hydrocarbon diluent to form a slurry of product solids; and (e) recovering the product metallocene solids. Preferred organolithium compounds have the formula, RLI.nLiX, where R is tert-alkyl, aryl, alkaryl, benzyl, or alkyl-substituted benzyl, or most preferably, methyl, and X is Br or I.

41 Claims, No Drawings

METALLOCENE SYNTHESIS

REFERENCE TO RELATED APPLICATION

This is a continuation-in-part of commonly-owned prior co-pending application Ser. No. 08/730,801, filed Oct. 17, 1996 now abandoned.

TECHNICAL FIELD

This invention relates to the production of metallocenes having in the molecule a Group 4 metal atom, two cyclopentadienyl-moiety-containing groups pi-bonded therewith and at least one, and preferably two, hydrocarbyl groups sigma-bonded therewith.

BACKGROUND

As is well known, Group 4 metal metallocenes are useful as ingredients or components for use in the formation of olefin polymerization catalyst systems. Considerable effort has been devoted to research on improving the efficacy of such materials and methods for their synthesis. Nevertheless, further improvements are needed in order to realize the full potential of these catalyst components, especially improvements relating to the synthesis of these metallocenes on a more efficient, less costly basis.

SUMMARY OF THE INVENTION

This invention provides a new, more efficient process for the preparation of a metallocene having one or two hydrocarbyl groups bonded to a Group 4 metal (hereinafter sometimes referred to as Metallocene II) from a dry or pasty crude mixture which contains a metallocene having two halogen atoms bonded to a Group 4 metal atom (hereinafter sometimes referred to as Metallocene I). The process enables use of crude Metallocene (I) compositions and thus eliminates time-consuming and costly separation procedures and attendant product losses. In addition, the process can substantially minimize undesirable side reactions leading to the formation of undesired co-products and reduced yields of the desired product. Indeed it is now possible pursuant to this invention to form Metallocene (II) of such purity that further conventional purification steps normally used often can be eliminated.

In one of its embodiments this invention provides a process which comprises:

a) mixing (i) liquid aromatic hydrocarbon, or a mixture of a major proportion by weight of liquid aromatic hydrocarbon and a minor proportion of liquid ether with (ii) a crude impure pasty or non-wet mixture containing at least 50% by weight of Metallocene (I) in whatever form or forms Metallocene (I) exists in such mixture, to form an anhydrous or substantially anhydrous first mixture;

b) mixing (i) a solution of an organolithium compound in an anhydrous ether solvent or paraffinic hydrocarbon solvent or a mixture thereof in whatever form or forms the organolithium compound exists in such solution, with (ii) the first mixture to form a second mixture, and agitating the second mixture for a period long enough for lithium halide solids to be formed by reaction in the second mixture; and c) separating the solids from the reaction mixture from b), or vice versa, and recovering the resultant liquid portion which consists essentially of a solution of Metallocene (II) in whatever form or forms Metallocene (II) exists while in said solution.

In another embodiment the above process which includes a) through c) as described immediately above, further comprises:

d) replacing all or substantially all of the original solvent from the solution from c) with a liquid paraffinic hydrocarbon diluent to form a slurry of which consists essentially of Metallocene (II) product solids in a liquid substantially paraffinic hydrocarbon diluent; and e) recovering said product solids.

In preferred embodiments, the above initial crude mixture is a reaction product mixture which contains as another main component lithium halide in whatever form or forms such a salt exists in such crude mixture. In the production of bridged or ansa-metallocenes, such crude mixtures of Metallocene (I) often contain lithium halide as a co-product, "contain" being used in the sense that upon workup of the reaction product it is possible to recover a lithium halide therefrom. This does not mean that the lithium halide must exist as lithium halide in the crude product—it may be wholly or partly ionized, or it may be complexed with one or more other materials and thus may not exist in the free state as lithium halide, or it may exist in the crude reaction mixture in some other altered form, state or condition.

In further preferred embodiments the Group 4 metal in Metallocenes (I) and (II) is zirconium or hafnium, and the amount of ether, if any, to which such Metallocenes (I) and (II) are exposed is kept to a minimum by not adding any ether to the mixture(s) being subjected to and formed in the process except to the extent the materials as received for use in the process may already contain one or more ether components.

In still further embodiments of this invention more stable organolithium compositions are used in the reaction with Metallocene I, and because of the use of such more stable organolithium compositions it is possible to achieve even higher yields of Metallocene (II). More particularly, in any of the above processes of this invention the organolithium compound is an organolithium complex with lithium bromide (RLi.nLiBr) or an organolithium complex with lithium iodide (RLi.nLiI). In these formulas n is 1 or a fractional number between 0 and 1.

These and other embodiments, features and advantages of this invention will become still further apparent from the ensuing description and appended claims.

FURTHER DETAILS AND DESCRIPTION OF PREFERRED EMBODIMENTS

Metallocene (I) when in isolated and pure form is a compound of the formula $$Q_n Cp^1 Cp^2 MX_2 \tag{I}$$

where:

Cp$^1$ and Cp$^2$ independently are cyclopentadienyl-moiety-containing groups, such as cyclopentadienyl, indenyl, fluorenyl or related group that can π-bond to the metal, or a hydrocarbyl, silyl, halo, halohydrocarbyl, hydrocarbylmetalloid, or halohydrocarbylmetalloid substituted derivative thereof, or any of the foregoing Cp groups having an additional hydrocarbon ring system fused thereon;

Q represents any bridging or ansa group that links the Cp groups;

M is a Group 4 metal atom;

X independently in each occurrence is a halogen atom; and n is either zero or 1.

Generally speaking, Metallocene (I) will contain in the range of 10 to about 75 carbon atoms in the molecule.

Metallocene (II) when in isolated and pure form is a compound of Formula (I) above with the exception that one and preferably each of the two X groups is replaced by a hydrocarbyl group which typically has in the range of 1 to about 12 carbon atoms. Preferably each such hydrocarbyl group is a methyl group, a tertiary alkyl group, an aryl group, a benzyl group, or a benzyl group having one or more hydrocarbyl substituents on the ring.

In most cases, Metallocenes (I) and (II) are racemic or chiral enantiomers, as compounds of such configurations are generally more useful for production of polypropylenes and other higher 1-olefin polymers of desired structural configurations. However nonracemic forms of Metallocenes (I) and (II) may be used and formed, respectively, in the process of this invention. For polymerization of ethylene, chiral metallocenes are not required.

Examples of metallocenes to which this invention is applicable include such compounds as:

bis(cyclopentadienyl)titanium dichloride;
bis(methylcyclopentadienyl)titanium dichloride;
bis(cyclopentadienyl)zirconium dichloride;
bis(methylcyclopentadienyl)zirconium dichloride;
bis(n-butylcyclopentadienyl)zirconium dichloride;
bis(dimethylcyclopentadienyl)zirconium dichloride;
bis(diethylcyclopentadienyl)zirconium dichloride;
bis(methyl-n-butylcyclopentadienyl)zirconium dichloride;
bis(n-propylcyclopentadienyl)zirconium dichloride;
bis(2-propylcyclopentadienyl)zirconium dichloride;
bis(methylethylcyclopentadienyl)zirconium dichloride;
bis(indenyl)zirconium dichloride;
bis(methylindenyl)zirconium dichloride;
bis(cyclopentadienyl)hafnium dichloride;
dimethylsilylenebis(indenyl)zirconium dichloride;
dimethylsilylenebis(methylindenyl)zirconium dichloride;
1,2-ethylenebis(indenyl)zirconium dichloride;
1,2-ethylenebis(methylindenyl)zirconium dichloride;
2,2-propylidenebis(cyclopentadienyl)(fluorenyl) zirconium dichloride;
dimethylsilylenebis(6-phenylindenyl)zirconium dichloride;

and analogous bromine and iodine derivatives. For identification of additional individual compounds that can serve as Metallocene (I) and thus constitute the precursor of Metallocene (II), one may refer, for example, to U.S. Pat. Nos. 5,153,157; 5,441,920 and 5,455,366, the entire disclosures of which are incorporated herein by reference.

For efficiency of operation the substantially anhydrous crude impure pasty or non-wet mixture will usually contain at least 50% by weight of Metallocene (I) in whatever form or forms Metallocene (I) exists in such mixture. Thus Metallocene (I) may exist in the crude mixture in free form, or it may be wholly or partly complexed, solvated or otherwise associated with other materials present in a reaction mixture or at least present at some stage of the synthesis reaction which led to the formation of this crude mixture. Likewise, depending of the synthesis method and the materials and conditions used in its synthesis, all or a portion of Metallocene (I) may be dissociated, ionized or otherwise placed in some other altered state, as long as Metallocene (II) can be recovered from the crude product by use of the process of this invention. In most cases the crude mixture is a reaction product mixture from a synthesis reaction in which Metallocene (I) is formed, whether or not the product mixture has been partially purified or worked up. However, other crude mixtures of Metallocene (I) can be subjected to the process of this invention. In short, this invention applies, and is intended to apply, to any crude mixture from which Metallocene (II) can be successfully recovered by the practice of this invention.

Thus the makeup or composition of the crude may vary but in general it should contain 50 wt % or more of Metallocene (I) in whatever form or forms Metallocene (I) exists in such reaction mixture, and one or more other materials such as one or more co-products formed in the reaction, and/or one or more raw materials and/or solvents or diluents not consumed in the reaction. When Metallocene (I) is a bridged or ansa metallocene, the crude reaction mixture will typically contain lithium halide co-product in whatever form or forms it may exist in such reaction mixture. Here again the precise chemical form adopted by the lithium halide is of no consequence as long as it can be successfully separated during the process so that a purified Metallocene (II) can be produced pursuant to this invention. Thus the lithium halide may be solvated, ionized, complexed, chelated, or etc., either in whole or in part as long as it can be successfully separated and removed during the process. When present, the lithium halide is usually present in an amount of at least about 10 wt % of the crude product.

As noted above, the crude reaction mixture when used in the process is either in the form of a paste (e.g., in a pasty, mushy or thick syrupy condition) or in the form of a non-wet (to the feel) loose or compacted solid material. Excessive amounts of solvents and diluents such as diethyl ether and/or toluene or the like should thus be removed from the reaction mixture before preparing the above first mixture.

To form the above first mixture, the solvent or diluent used is either (a) one or more liquid aromatic hydrocarbons, or (b) a mixture composed of a major amount (more than 50% by weight) one or more liquid aromatic hydrocarbons together with a minor amount (less than 50% by weight) of one or more liquid ethers. Preferably at least about 90% by weight of the total liquid phase in the first mixture is composed of such aromatic hydrocarbon(s) with or without such ether(s). The balance, if any, of the solvent or diluent making up the liquid phase of the first mixture can be any other innocuous solvent such as one or more liquid paraffinic hydrocarbons, one or more liquid cycloparaffinic hydrocarbons, or the like, including mixtures of such paraffin(s) and cycloparaffin(s). Since the reaction to form Metallocene (II) involves use of an organolithium reactant the first mixture should be anhydrous or at least substantially anhydrous (e.g., it should contain, if any, not more than about 50 ppm (wt/wt) of water). Thus the foregoing solvents or diluents used in forming the first mixture should be anhydrous or sufficiently low in water content to result in an anhydrous or substantially anhydrous first mixture. The amount of aromatic hydrocarbon in the solvent or diluent used should be at least about 10 times the weight of the crude reaction mixture being processed, and typically the weight ratio of aromatic hydrocarbon to the crude mixture being processed will fall in the range of about 5:1 and about 50:1.

The mode and order of addition of the components in forming the first mixture is not critical. The mixing can be performed under ambient temperature conditions and moderate heating can be used to facilitate the mixing, if desired. Good agitation should be utilized, and thus vessels equipped with mechanical stirrers or agitators are preferably employed in this operation. Benzene, toluene, m-xylene, p-xylene, ethylbenzene, tetrahydronaphthalene, and mixtures such as mixed xylenes, benzene-toluene-xylene mixtures, and similar liquid aromatic hydrocarbons can be and preferably are used in forming the first mixture, especially when the Group 4 metal of Metallocene (I) is hafnium. When the Group 4 metal of Metallocene (I) is titanium or zirconium, either (a) one or more liquid aromatic hydrocarbons alone, or (b) a mixture of one or more liquid aromatic hydrocarbons together with one or more liquid monoethers or polyethers, whether cyclic or acyclic can be used. Examples of such ethers include diethyl ether, methyl-tert-butyl ether, dibutyl ether, diamyl ether, ethyl tert-butyl ether, methyl tert-amyl ether, tetrahydrofuran, 2-methylhydrofuran, 3-methyltetrahydrofuran, tetrahydropyran, 1,3-dioxolane, 1,4-dioxane, ethylene glycol dimethyl ether, ethylene glycol diethyl ether, and similar liquid ethers. When the Group 4 metal of Metallocene (I) is zirconium or especially hafnium, a mixture of one or more liquid ethers with one or more liquid aromatic hydrocarbons can be used provided the particular metallocene and the ether do not react with each other to form an excessive amount of undesirable co-product(s). In this regard, it has been found that undesirable side reactions tend to occur when Metallocene (I) is a bridged zirconocene or bridged hafnocene and certain ethers, especially cyclic ethers such as tetrahydrofuran are present therewith in substantial amounts during the reaction. The nature and extent of these adverse reactions has not been studied in any detail. All that can be stated at this point in time is that tetrahydrofuran itself should not be used in high concentration (e.g., more than about 5 wt %) in a liquid solvent mixture at least with certain bridged metallocenes such as rac-1,1'-dimethylsilanylenebis (indenyl)hafnium dichloride (also known as rac-1,1'-dimethylsilylbisindenylhafnium dichloride) lest adverse side reactions occur. Thus it is prudent in any similar situation to make a preliminary test to determine whether a proposed bridged zirconium or hafnium metallocene and the cyclic ether plus aromatic hydrocarbon can be used together under the proposed conditions without significant loss of the metallocene through undesirable side reactions. It is to be noted that insignificant amounts (e.g., up to about 5 wt % or so) of tetrahydrofuran can be tolerated in the solvent system even with rac-1,1'-dimethylsilylbisindenylhafnium dichloride, albeit the presence of this ether therewith is not recommended.

A solution of an organolithium compound in an anhydrous ether or paraffinic hydrocarbon solvent or a mixture thereof in whatever form or forms the organolithium compound exists in such solution is combined with the first mixture under conditions such that replacement of one or both of the halogen atoms of Metallocene (I) by a hydrocarbyl group takes place. The exact reaction mechanism of this reaction is unimportant, and the precise chemical forms of the reactants in the reaction mixture before and during the reaction is irrelevant so long as upon completion of the process of this invention the end product is at least in part, and preferably preponderately, Metallocene (II). This operation is typically conducted at one or more temperatures above about 15° C. Usually there is no need to exceed a temperature above about 75° C. but any temperature below the thermal decomposition and/or sublimation temperatures of Metallocenes (I) and (II) can be used, should this prove necessary or desirable under a given set of circumstances. In most cases at least a substantial portion of the reaction will be performed at one or more temperatures in the range of about 20° C. to about 50° C. For example, during, say, at least about one-half of the total reaction period between the organolithium reactant and Metallocene (I), it is preferable to maintain the temperature of this reaction mixture within the range of about 20 to about 50° C. This reaction can be, and preferably is, conducted in the same vessel as that in which the first mixture was formed. For best results, the reaction mixture should be stirred or otherwise agitated during the course of the reaction. Reaction times may vary but typically fall in the range of 0.5 to about 48 hours, and preferably in the range of about 0.5 to about 4 hours. Lithium halide is formed as a co-product in this reaction and thus typically appears as solids in the mixture. If the organolithium compound is to be used as a solution with one or more ethers and if Metallocenes (I) and (II) are bridged hafnium metallocenes, for the same reasons as described above, tetrahydrofuran and/or any other cyclic ether that would cause adverse side reactions to occur at the selected reaction temperature(s) should not be used as, or in, the solvent for the organolithium compound. Insignificant amounts of such cyclic ethers (e.g., up to about 5 wt % or so) in an otherwise innocuous solvent apparently can be tolerated in such situations, however.

Typically the organolithium compound has in the range of 1 to about 12 carbon atoms in the molecule, but higher molecular weight organolithium compounds can be used if desired. Preferred organolithium compounds include, for example, tert-butyllithium, tert-amyllithium, neo-pentyllithium, phenyllithium, o-tolyllithium, m-tolyllithium, p-tolyllithium, 2,4-xylyllithium, 4-biphenylyllithium, benzyllithium, p-methylbenzyllithium, p-ethylbenzyllithium, 1-naphthyllithium, and 2-naphthyllithium. Methyllithium is a particularly preferred reactant. Examples of paraffinic solvents for the organolithium compound include n-pentane, n-hexane, 2-methylpentane, 3-methylpentane, n-heptane, 2,2-dimethylpentane, 2,3-dimethylpentane, 2,4-dimethylpentane, 3,3-dimethylpentane, 3-ethylpentane, 2-methylhexane, 3-methylhexane, n-octane, 2-methylheptane, 4-methylheptane, 2,3-dimethylhexane, 2,4-dimethylhexane, 2,5-dimethylhexane, 3,4-dimethylhexane, 3-ethylhexane, 2,2,4-trimethylpentane, 3-ethyl-2-methylpentane, n-nonane, 2,6-dimethylheptane, cyclohexane, methylcyclopentane, methylcyclohexane and cycloheptane. Mixtures or two or more such paraffinic hydrocarbons can also be used. Subject to the above caveat regarding avoidance or minimization of amounts of certain cyclic ethers with hafnocenes, ethers which can be used as solvents for the organolithium compound can be cyclic or acyclic monoethers or polyethers. Dihydrocarbyl ethers such as diethyl ether are desirable ether solvents for use in forming solutions of methyllithium.

As noted above, it is especially desirable pursuant to this invention to employ as the organolithium reactant, a lithium bromide or lithium iodide complex thereof which contains up to about 1 mole of LiX per mole of RLi, such as, for example, methyllithium-lithium bromide complex (MeLi.nLiBr), methyllithium-lithium iodide complex (MeLi.nLiI), and similar complexes with other organolithium compounds such as those identified above. In the formulas of the lithium complexes as they may appear anywhere in this specification or in the claims hereof, X is Br or I, and n is 1 or any fraction between 0 and 1. Often n is at least 0.1. These complexes tend to exhibit greater thermal stability than the corresponding non-complexed organolithium compound, and in addition, in at least some cases provide higher yields of Metallocene (II).

The proportions of organolithium compound relative to Metallocene (I) should be such as to replace one or both (as desired) of the halogen atoms of Metallocene (I) into one or two hydrocarbyl groups. Thus a slight excess of organolithium compound over the stoichiometric amount for the desired reaction is typically used, and preferably the organolithium compound is added in incremental portions, and the addition is terminated when an optimum conversion to the Metallocene (II) desired has been achieved.

After completing the reaction of an organolithium compound of the RLi type and Metallocene (I), the solids are separated from the resultant reaction mixture, or vice versa, by use of such procedures as filtration, decantation and/or centrifugation, and the liquid portion is recovered. This liquid phase consists essentially of a solution of Metallocene (II) in whatever form or forms Metallocene (II) exists while in this solution. The solvent(s) in this solution are predominately the aromatic hydrocarbon(s) with or without ether(s) used in forming the original first mixture together with some other material(s) initially present in the crude product being processed, and the paraffinic and/or ether solvent for the organolithium compound. While the same separation and recovery sequence can be applied to the reaction mixture in which the organolithium compound used was of the RLi.nLiBr or RLi.nLiI type, it is desirable to first remove, e.g., by distillation, any ether that is present in the reaction mixture and then subject the residual hydrocarbonaceous slurry to filtration or like solids-liquid separation procedure, thereby providing a solution of Metallocene (II) in a substantially ether-free hydrocarbon solvent.

At this point, a solvent replacement or solvent exchange procedure, (sometimes referred to as a "solvent swap"), may be carried out, if desired. In this operation two things may be done either concurrently or sequentially. These two things are: (1) removing from the reaction mixture substantially all of the original solvent (and associated dissolved impurities, etc.) and (2) substituting for the original solvent a liquid paraffinic hydrocarbon diluent. Thus, if operations (1) and (2) are done concurrently the paraffinic diluent is added to the reaction mixture as the original solvent is being removed therefrom. If done sequentially, the better practice is to remove the original solvent and then add the paraffinic diluent. In either case a slurry or suspension of product solids in the paraffinic diluent is formed. This operation is best conducted so as to minimize the extent to which the Metallocene (II) may be dissolved in the paraffinic diluent. Thus operation at room temperature or even lower temperatures is desirable. An alternative procedure which may be used in lieu of the "solvent swap" procedure is to distill off a substantial portion of the aromatic solvent to leave a thick, concentrated slurry of Metallocene (II) solids in the aromatic solvent which tends to contain dissolved impurities as well as some Metallocene (II). The purer Metallocene (II) solids are recovered from this concentrated slurry by filtration or other suitable solids-liquid separation technique.

Liquid substantially paraffinic hydrocarbon diluents suitable for conducting the solvent exchange operation typically contain in the range of from about 6 to about 30 carbon atoms. They can be a single pure saturated hydrocarbon or a mixture of saturated hydrocarbons (paraffins or cycloparaffins or mixtures thereof). The solids (which usually are Metallocene (II) in substantially pure form) are the separated by decantation, filtration and/or centrifugation. The solids so recovered are preferably washed with a liquid alkane having in the range of from about 5 to about 10 carbon atoms and air or oven dried. Usually further purification is unnecessary. However, if desired the Metallocene (II) product may be further purified for example by crystallization from a suitable solvent.

The following examples illustrate procedures for conducting the process of this invention. The examples are not intended to limit, and should not be construed as limiting, the invention to the specific details set forth therein.

EXAMPLE 1

Rac-1,1-dimethylsilylbisindenylhafnium dichloride (4.93 g of 82 wt % purity; 7.54 mmol) was placed in a 200 mL Schlenk flask with 56.7 g of toluene. Most of the orange-yellow metallocene remained undissolved. The slurry was heated to 34° C. and a solution of MeLi.nLiBr (1.5M in ether) was added dropwise over two hours. The solution became yellow-orange and the solids lightened to a beige color. The reaction was allowed to cool to ambient temperature and stir overnight. NMR analysis revealed high purity product with only 2.5 mol % of monomethyl intermediates. The lithium salts were removed by filtration on a medium frit and washed with toluene. The combined filtrates were stripped to a dry residue in vacuo. The residue was triturated with 15 mL of heptane, filtered, and the solids dried in vacuo. This material was extracted with toluene and refiltered to remove a small amount of dark insolubles. The filtrate was again stripped to dryness, triturated with heptane (17 mL), and the product was filtered. The yellow solids were dried in vacuo. The yield of rac-dimethylsilylbisindenylhafnium dimethyl was 3.11 g (83%).

EXAMPLE 2

Diphenylmethylidene(cyclopentadienyl)(9-fluorenyl) hafnium dichloride (4.35 g of 73.4 wt % purity, 4.96 mmol) was suspended in 132 g of toluene. Most of the orange-yellow metallocene remained undissolved. A solution of MeLi.nLiBr (5.87 wt % in ether, 3.77 g) was added dropwise over 25 minutes. The solution became yellow-orange and the solids lightened. Analysis of the reaction, showed 36.5% partially alkylated intermediate. Additional aliquots of MeLi.nLiBr (1.18 g total) were added dropwise until the monomethyl intermediate was not detectable. The lithium salts were removed by filtration on a medium frit and washed with toluene. The combined filtrates were stripped to approximately a quarter of the volume in vacuo. The yellow slurry was diluted with 13.7 g of hexanes and filtered on a medium frit. The solids were washed with 3.4 g of hexanes and dried in vacuo. The yield of diphenylmethylidene (cyclopentadienyl)(9-fluorenyl)hafnium dimethyl product was 2.31 g (77%).

EXAMPLE 3

Rac-1,1-dimethylsilylbis(2-methylindenyl)zirconium dichloride (5.03 g, 10.55 mmol) was suspended in 100 g of toluene. The orange slurry was heated in an oil bath to 40° C. Most of the orange-yellow metallocene remained undissolved. MeLi.nLiBr (5.87 wt % in ether, 7.78 g) was added dropwise over two hours. The solution became amber/yellow and the solids lightened. The reaction was allowed to cool to ambient temperature and stir overnight. Analysis of the reaction, showed 9.3 mol % of mono-methyl intermediates. Additional aliquots of MeLi.nLiBr (1.66 g) were added dropwise until the monomethyl intermediates were reduced to less than two mol %. Approximately a quarter of the solvent was removed in vacuo and then the lithium salts were filtered on a medium frit and washed with 20 mL of toluene. The combined filtrates were concentrated in vacuo. A yellow crystalline solid formed. The slurry was cooled to −20° C. The yellow crystals were filtered on a coarse frit. After drying in vacuo, the yield of rac-dimethylsilylbis(2-methylindenyl)zirconium dimethyl was 3.20 g (70%).

EXAMPLE 4

Rac-1,1-dimethylsilylbisindenylhafnium dichloride (5.02 g of 78 wt % purity; 7.31 mmol) was placed in a 200 mL Schlenk flask with 59.1 g of toluene. Most of the orange-yellow metallocene remained undissolved. The slurry was heated to 35° C. and 9.5 mL of MeLi solution (1.4 M in ether, halide ~0.05 M) were added dropwise over two hours. The solution became amber and the solids became a light brown color. The reaction was allowed to cool to ambient temperature. Analysis revealed 57 mol % monomethyl intermediate and no starting material. Additional aliquots of MeLi (3.5 mL) were added dropwise and the monomethyl intermediate was reduced to less than one mol %. Approximately a quarter of the solvent was removed in vacuo and then the lithium salts were filtered on a medium frit and washed with 10 mL of toluene. The combined filtrates were stripped to a dry residue in vacuo. This material was extracted with 49 g of toluene and refiltered to remove a small amount of dark insolubles. The filtrate was stripped nearly to dryness, triturated with heptane (15 mL), and the product was filtered on a coarse frit. The solids were dried in vacuo. The yield of rac-dimethylsilylbisindenylhafnium dimethyl was 2.73 g (75%).

EXAMPLE 5

Under a nitrogen atmosphere, 4.65 g (6.37 mmols) of a crude racemic 1,1'-dimethylsilylbisindenylhafnium dichloride ("HDC") product mixture (an anhydrous solid containing 73.3 wt % HDC (by NMR) and the balance mostly being LiCl) and 27 g of anhydrous toluene were charged into a 100 cc flask. The toluene thus contained about 14.7 wt % crude product and about 11.2 wt % of contained HDC. After the slurry was stirred at ambient temperature (25–26° C.) for 5 minutes, 7.17 g (12.75 mmols) of a 1.28 M slurry of methyllithium (MeLi) in diethylether ($Et_2O$) in a dropping funnel was fed for 15 minutes. The resultant slurry was heated up to and stirred at about 35° C. for 3 hours. The flask/reactor was moved to a dry box and a sample of the reaction slurry was taken for NMR analysis. The reaction mass was then vacuum filtered and the wet cake (mainly LiCl) was washed with 10 g of toluene. The filtrate was vacuum-stripped to remove $Et_2O$/toluene and a total of 7.3 g of nonane was added to the flask to effect a solvent replacement or "solvent-swap". The resultant slurry in nonane was filtered and the wet cake was washed with 1 g of hexane to facilitate drying. 3.11 Grams of dried crude 1,1'-dimethylsilylbisindenylhafnium dimethyl product were obtained as light yellow particles or powder.

EXAMPLE 6

Under a nitrogen pad, 3.11 g (4.26 mmols) of anhydrous crude HDC (73.3 wt % HDC and balance mostly being LiCl) and 27 g of toluene were stirred in a 100 cc flask for 10 minutes. 4.80 Grams (8.53 mmols) of 1.28 M MeLi in diethyl ether was fed for 20 minutes. The slurry was stirred at ambient temperature for about 6 hours. After taking a sample for NMR analysis, the reaction mass was stirred for 18 more hours. 5 Grams of toluene were added and ether was stripped off under reduced pressure. The slurry was filtered to remove solids (mainly LiCl) and 5 g of toluene was used to wash the solids. To the filtrate 2 g of nonane was added. Toluene was stripped off under reduced pressure. 3 Grams of nonane was added during the solvent exchange. The resultant slurry was filtered, washed with 1 g of hexane and dried to obtain 2.00 g of crude 1,1'-dimethylsilylbisindenylhafnium dimethyl product.

EXAMPLE 7A

In a dry box, 1.53 g (2 mmols) of crude HDC (70.7 wt % HDC and the balance mostly being LiCl) were slurried in 10 g of $Et_2O$ in a 50 cc flask. 2.06 Grams (4 mmols) of 1.4 M MeLi in $Et_2O$ was added over about 2 minutes and the reaction mixture was stirred at ambient temperature for about 7 hours. A dry, pale-yellow solid was then obtained by evaporating solvent off under vacuum.

Comparative Example 7B

In a dry box, 2.57 g (3.4 mmols) of crude HDC (70.7 wt % HDC; yellow solids) was charged into a 100 cc flask. 10 Grams of tetrahydrofuran ("THF") was added and a black solution was obtained. The pressure was immediately reduced to remove most of the THF, and this left a wet, dark-colored solid. 16 Grams of $Et_2O$ were added to obtain a yellow slurry. 4.0 Grams (7.8 mmol) of 1.4 M MeLi in Et2O were added. The reaction slurry (still a yellow slurry after ~30 minutes of stirring) was stirred at ambient temperature overnight for about 15.5 hours. A "relatively clean" ether solution was decanted from a black solid stuck on the flask. NMR showed that the solid was a highly impure material.

EXAMPLE 8

Under a nitrogen pad, 0.1 g of 1.4 M MeLi in $Et_2O$ was added to 40 g of toluene (to further dry the solvent). 1.12 Grams (1.67 mmols) of crude HDC (80 wt % HDC) and 10 grams of toluene were added. 1.72 Grams (3.34 mmols) of 1.4 M MeLi in $Et_2O$ was added during about 5 minutes at ambient temperature. After taking samples for NMR analysis at 2 and 19 hours, 0.14 gram (0.27 mmol) of the MeLi solution was added at 20.5 hours. Two additional samples were taken at 24 and 43.5 hours. These analyses indicated that the amount of 1,1'-dimethylsilylbisindenylhafnium dimethyl formed increased over time.

EXAMPLE 9

In this operation a 1,1'-dimethylsilylbisindenylhafnium dimethyl product was formed as follows: 0.1 Gram of 1.4 M MeLi in $Et_2O$ was added to 35 g toluene in a 100 cc flask. 1.04 Grams (1.5 mmols) of crude HDC (77 wt %) and 10 g of toluene were added. The slurry was cooled to 0.9° C. 1.7 Grams (3.3 mmols) of the MeLi solution and 5 g of toluene were fed at about 0.9–1.6° C. for 25 minutes. The reaction mass was stirred at 1.6–7.6° C. for about 21 hours and then warmed to ambient temperature.

EXAMPLE 10

3.5 Grams (5.04 mmols) of crude HDC (77 wt %) was slurried in 17 g of toluene. 5.96 Grams (11.59 mmols) of 1.4 M MeLi in $Et_2O$ and 5 g of toluene were fed at 2.8–3.8° C. for 50 minutes. The reaction mass was stirred at 7.3–7.8° C. for 45 hours. The slurry was then filtered and 12 g of toluene was used to wash the cake. After most of the toluene had been vacuum-stripped off from the filtrate, 9 g of nonane was added and vacuum stripping was continued for further removal of toluene. The resultant slurry was filtered. The solid filter cake was washed with 1 g of hexane and dried to yield 2.00 grams of crude 1,1'-dimethylsilylbisindenylhafnium dimethyl product.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a chemical reaction, complex formation, solvation, ionization, or other transformation during the course of contacting, blending or mixing operations, if done in accordance with the disclosure hereof, is within the purview and scope of this invention.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for the preparation of a metallocene having one or two hydrocarbyl groups bonded to a Group 4 metal (hereinafter sometimes referred to as Metallocene II) from a metallocene having two halogen atoms bonded to a Group 4 metal atom (hereinafter sometimes referred to as Metallocene I), which process comprises:
   a) mixing (i) liquid aromatic hydrocarbon, or a mixture of a major proportion by weight of liquid aromatic hydrocarbon and a minor proportion of liquid ether with (ii) a crude impure pasty or non-wet mixture containing at least 50% by weight of Metallocene I in whatever form or forms Metallocene I exists in such mixture, and additionally containing at least about 10 wt % lithium halide in whatever form or forms it exists in said pasty or non-wet mixture, to form an anhydrous or substantially anhydrous first mixture;
   b) mixing (i) a solution of an organolithium compound in an anhydrous ether solvent or paraffinic hydrocarbon solvent or a mixture thereof in whatever form or forms the organolithium compound exists in such solution, with (ii) the first mixture to form a second mixture, and agitating the second mixture for a period long enough for lithium halide solids to be formed by reaction in the second mixture; and
   c) separating the solids from the mixture from b), or vice versa, and recovering the resultant liquid portion which consists essentially of a solution of Metallocene II in whatever form or forms Metallocene II exists while in said solution.

2. A process according to claim 1 wherein b) is performed at one or more temperatures in the range of about 20° C. to about 50° C. and for a period in the range of about 0.5 to about 48 hours.

3. A process according to claim 1 wherein (i) of a) is a single liquid aromatic hydrocarbon or a mixture of liquid aromatic hydrocarbons.

4. A process according to claim 1 wherein the organolithium compound of solution (i) of b) is methyllithium in whatever form or forms it exists in said solution.

5. A process according to claim 1 wherein the two halogen atoms of Metallocene I are chlorine atoms, and a sufficient quantity of organolithium compound solution is used to result in replacement of the two chlorine atoms of Metallocene I by two hydrocarbyl groups.

6. A process according to claim 1 wherein the Group 4 metal atom of Metallocene I is a hafnium atom and wherein (i) of a) is one or a mixture of liquid aromatic hydrocarbons.

7. A process according to claim 1 wherein the Group 4 metal atom of Metallocene I is a zirconium atom and wherein (i) of a) is a liquid ether having a saturated furan ring system, or is a mixture of liquid ethers more than 50% by weight of which is one or more liquid ethers having a saturated furan ring system.

8. A process for the preparation of a metallocene having one or two hydrocarbyl groups bonded to a Group 4 metal (hereinafter sometimes referred to as Metallocene II) from a metallocene having two halogen atoms bonded to a Group 4 metal atom (hereinafter sometimes referred to as Metallocene I), which process comprises:
   a) mixing (i) liquid aromatic hydrocarbon, or a mixture of a major proportion by weight of liquid aromatic hydrocarbon and a minor proportion of liquid ether with (ii) a crude impure pasty or non-wet reaction mixture containing at least 50% by weight of Metallocene I in whatever form or forms Metallocene I exists in such reaction mixture, and additionally containing at least about 10 wt % lithium halide in whatever form it exists in said pasty or non-wet mixture, to form an anhydrous or substantially anhydrous first mixture;
   b) mixing (i) a solution of an organolithium compound in an anhydrous ether solvent or paraffinic hydrocarbon solvent or a mixture thereof in whatever form or forms the organolithium compound exists in such solution, with (ii) the first mixture to form a second mixture, and agitating the second mixture for a period long enough for lithium halide solids to be formed by reaction in the second mixture;
   c) separating the solids from the mixture from b), or vice versa, and recovering the resultant liquid portion which consists essentially of a solution of Metallocene II in whatever form or forms Metallocene II exists while in said solution;
   d) replacing all or substantially all of the original solvent of the solution from c) with a liquid paraffinic hydrocarbon diluent to form a slurry which consists essentially of Metallocene II product solids in a liquid substantially paraffinic hydrocarbon diluent; and
   e) recovering said product solids.

9. A process according to claim 8 wherein b) is performed at one or more temperatures in the range of about 20° C. to about 50° C. and for a period in the range of about 0.5 to about 48 hours.

10. A process according to claim 8 wherein (i) of a) is a single liquid aromatic hydrocarbon or a mixture of liquid aromatic hydrocarbons.

11. A process according to claim 8 wherein the organolithium compound of solution (i) of b) is methyllithium in whatever form or forms it exists in said solution.

12. A process according to claim 8 wherein the two halogen atoms of Metallocene I are chlorine atoms, and a sufficient quantity of organolithium compound solution is used to result in replacement of the two chlorine atoms of Metallocene I by two hydrocarbyl groups.

13. A process according to claim 8 wherein the Group 4 metal atom of Metallocene I is a hafnium atom and wherein (i) of a) is one or a mixture of liquid aromatic hydrocarbons.

14. A process according to claim 8 wherein the Group 4 metal atom of Metallocene I is a zirconium atom and wherein (i) of a) is a mixture of a major proportion by weight of one or a mixture of liquid aromatic hydrocarbons and a minor proportion by weight of one or more liquid ethers.

15. A process according to claim 8 wherein Metallocene I is at least one metallocene compound which if isolated and purified would have the formula $Q_nCp^1Cp^2MX_2$ where:

Cp¹ and Cp² can be the same or different and each is a cyclopentadienyl, indenyl, fluorenyl or related group that can π-bond to the metal, or a hydrocarbyl, silyl, halo, halohydrocarbyl, hydrocarbylmetalloid, or halohydrocarbylmetalloid substituted derivative thereof, or any of the foregoing Cp groups having an additional hydrocarbon ring system fused thereon;

Q represents any bridging or ansa group that links the Cp groups;

M is a Group 4 metal atom;

X independently in each occurrence is a halogen atom; and n is either zero or 1.

16. A process according to claim 15 wherein n is 1.

17. A process according to claim 15 wherein n is 1 and Q is a dimethylsilyl group, $(CH_3)_2Si<$.

18. A process according to claim 15 wherein M is a hafnium atom, and wherein (i) of a) is one or a mixture of liquid mononuclear aromatic hydrocarbons.

19. A process according to claim 15 wherein Metallocene I is 1,1'-dimethylsilylbisindenylhafnium dichloride.

20. A process according to claim 15 wherein the organolithium compound is methyllithium, and a sufficient quantity of methyllithium solution is used to result in replacement of the two halogen atoms of Metallocene I by two methyl groups.

21. A process according to claim 15 wherein Metallocene I is rac-1,1'-dimethylsilylbisindenylhafnium dichloride; wherein (i) of a) is predominately toluene; and wherein the solution of organolithium compound is a solution of methyllithium employed in sufficient quantity to result in replacement of the two chlorine atoms of 1,1'-dimethylsilylbisindenylhafnium dichloride by two methyl groups.

22. A process for the preparation of a metallocene having one or two hydrocarbyl groups bonded to a Group 4 metal (hereinafter sometimes referred to as Metallocene II) from a metallocene having two halogen atoms bonded to a Group 4 metal atom (hereinafter sometimes referred to as Metallocene I), which process comprises:

a) mixing (i) liquid aromatic hydrocarbon, or a mixture of a major proportion by weight of liquid aromatic hydrocarbon and a minor proportion of liquid ether with (ii) a crude impure pasty or non-wet mixture containing at least 50% by weight of Metallocene I in whatever form or forms Metallocene I exists in such mixture, to form an anhydrous or substantially anhydrous first mixture;

b) mixing (i) a solution of an organolithium compound in an anhydrous ether solvent or paraffinic hydrocarbon solvent or a mixture thereof, said organolithium compound having the formula, RLi.nLiX, where R is methyl, tertiary alkyl, aryl, alkaryl, benzyl, or alkyl-substituted benzyl, n is 1 or a fractional number between 0 and 1, and X is a bromine or iodine atom, and wherein said organolithium compound is in whatever form or forms said organolithium compound exists in such solution, with (ii) the first mixture to form a second mixture, and agitating the second mixture for a period long enough for lithium halide solids to be formed by reaction in the second mixture; and c) separating the solids from the mixture from b), or vice versa, and recovering the resultant liquid portion which consists essentially of a solution of Metallocene II in whatever form or forms Metallocene II exists while in said solution.

23. A process according to claim 22 wherein the substantially anhydrous crude impure pasty or non-wet mixture (ii) of a) additionally contains at least about 10 wt % lithium halide in whatever form or forms it exists in said pasty or non-wet mixture.

24. A process according to claim 22 wherein b) is performed at one or more temperatures in the range of about 20° C. to about 50° C. and for a period in the range of about 0.5 to about 24 hours.

25. A process according to claim 22 wherein (i) of a) is a single liquid aromatic hydrocarbon or a mixture of liquid aromatic hydrocarbons.

26. A process according to claim 22 wherein the organolithium compound of solution (i) of b) is $CH_3Li.nLiBr$ or $CH_3Li.nLiI$ in whatever form or forms it exists in said solution.

27. A process according to claim 22 wherein the two halogen atoms of Metallocene I are chlorine atoms, and a sufficient quantity of organolithium compound solution is used to result in replacement of the two chlorine atoms of Metallocene I by two hydrocarbyl groups.

28. A process according to claim 22 wherein the Group 4 metal atom of Metallocene I is a hafnium atom and wherein (i) of a) is one or a mixture of liquid aromatic hydrocarbons.

29. A process according to claim 22 wherein the Group 4 metal atom of Metallocene I is a zirconium atom and wherein (i) of a) is one or a mixture of liquid aromatic hydrocarbons.

30. A process according to claim 22 wherein Metallocene I is rac-1,1'-dimethylsilylbis(indenyl)hafnium dichloride, and wherein (i) of a) is a single liquid aromatic hydrocarbon or a mixture of liquid aromatic hydrocarbons.

31. A process according to claim 30 wherein the organolithium compound of solution (i) of b) is $CH_3Li.nLiBr$ or $CH_3Li.nLiI$ in whatever form or forms it exists in said solution.

32. A process according to claim 22 wherein Metallocene I is diphenylmethylidene(cyclopentadienyl)9-fluorenyl) hafnium dichloride, and wherein (i) of a) is a single liquid aromatic hydrocarbon or a mixture of liquid aromatic hydrocarbons.

33. A process according to claim 32 wherein the organolithium compound of solution (i) of b) is $CH_3Li.nLiBr$ or $CH_3Li.nLiI$ in whatever form or forms it exists in said solution.

34. A process according to claim 22 wherein Metallocene I is rac-1,1'-dimethylsilylbis(methylindenyl)zirconium dichloride, and wherein (i) of a) is a single liquid aromatic hydrocarbon or a mixture of liquid aromatic hydrocarbons.

35. A process according to claim 34 wherein the organolithium compound of solution (i) of b) is $CH_3Li.nLiBr$ or $CH_3Li.nLiI$ in whatever form or forms it exists in said solution.

36. A process for the preparation of a metallocene having one or two hydrocarbyl groups bonded to a zirconium atom (hereinafter referred to as Zirconocene II) from a metallocene having two halogen atoms bonded to a zirconium atom (hereinafter referred to as Zirconocene I), which process comprises:

a) mixing (i) a liquid ether having a saturated furan ring system, or a mixture of liquid ethers more than 50% by weight of which is one or more liquid ethers having a saturated furan ring system (ii) a crude impure pasty or non-wet mixture containing at least 50% by weight of Zirconocene I in whatever form or forms Zirconocene I exists in such mixture, to form an anhydrous or substantially anhydrous first mixture;

b) mixing (i) a solution of an organolithium compound in an anhydrous ether solvent or paraffinic hydrocarbon solvent or a mixture thereof in whatever form or forms the organolithium compound exists in such solution, with (ii) the first mixture to form a second mixture, and agitating the second mixture for a period long enough for lithium halide solids to be formed by reaction in the second mixture; and c) separating the solids from the mixture from b), or vice versa, and recovering the resultant liquid portion which consists essentially of a solution of Zirconocene II in whatever form or forms Zirconocene II exists while in said solution.

37. A process for the preparation of a metallocene having one or two hydrocarbyl groups bonded to a hafnium atom (hereinafter referred to as Hafnocene II) from a metallocene having two halogen atoms bonded to a hafnium atom (hereinafter referred to as Hafnocene I), which process comprises:

a) mixing (i) one or a mixture of liquid aromatic hydrocarbons with (ii) a crude impure pasty or non-wet reaction mixture containing at least 50% by weight of Hafnocene I in whatever form or forms Hafnocene I exists in such reaction mixture, to form an anhydrous or substantially anhydrous first mixture;

b) mixing (i) a solution of an organolithium compound in an anhydrous ether solvent or paraffinic hydrocarbon solvent or a mixture thereof in whatever form or forms the organolithium compound exists in such solution, with (ii) the first mixture to form a second mixture, and agitating the second mixture for a period long enough for lithium halide solids to be formed by reaction in the second mixture;

c) separating the solids from the mixture from b), or vice versa, and recovering the resultant liquid portion which consists essentially of a solution of Hafnocene II in whatever form or forms Hafnocene II exists while in said solution;

d) replacing all or substantially all of the original solvent of the solution from c) with a liquid paraffinic hydrocarbon diluent to form a slurry which consists essentially of Hafnocene II product solids in a liquid substantially paraffinic hydrocarbon diluent; and e) recovering said product solids.

38. A process for the preparation of a metallocene having one or two hydrocarbyl groups bonded to a zirconium atom (hereinafter referred to as Zirconocene II) from a metallocene having two halogen atoms bonded to a zirconium atom (hereinafter referred to as Zirconocene I), which process comprises:

a) mixing (i) liquid aromatic hydrocarbon, or a mixture of a major proportion by weight of liquid aromatic hydrocarbon and a minor proportion of one or more liquid ethers with (ii) a crude impure pasty or non-wet reaction mixture containing at least 50% by weight of Zirconocene I in whatever form or forms Zirconocene I exists in such reaction mixture, to form an anhydrous or substantially anhydrous first mixture;

b) mixing (i) a solution of an organolithium compound in an anhydrous ether solvent or paraffinic hydrocarbon solvent or a mixture thereof in whatever form or forms the organolithium compound exists in such solution, with (ii) the first mixture to form a second mixture, and agitating the second mixture for a period long enough for lithium halide solids to be formed by reaction in the second mixture;

c) separating the solids from the mixture from b), or vice versa, and recovering the resultant liquid portion which consists essentially of a solution of Zirconocene II in whatever form or forms Zirconocene II exists while in said solution;

d) replacing all or substantially all of the original solvent of the solution from c) with a liquid paraffinic hydrocarbon diluent to form a slurry which consists essentially of Zirconocene II product solids in a liquid substantially paraffinic hydrocarbon diluent; and e) recovering said product solids.

39. A process for the preparation of a metallocene having one or two hydrocarbyl groups bonded to a Group 4 metal (hereinafter referred to as Metallocene II) from a metallocene having two halogen atoms bonded to a Group 4 metal atom and which if isolated and purified would have the formula $$Q_n Cp^1 Cp^2 MX_2$$

where:

Cp$^1$ and Cp$^2$ can be the same or different and each is a cyclopentadienyl, indenyl, fluorenyl or related group that can π-bond to the metal, or a hydrocarbyl, silyl, halo, halohydrocarbyl, hydrocarbylmetalliod, or halohdrocarbylmetalloid substituted derivative thereof, or any of the foregoing Cp groups having an additional hydrocarbon ring system fused thereon;

Q is a dimethylsilyl group, $(CH_3)_2Si<$;

M is a Group 4 metal atom;

X independently in each occurrence is a halogen atom; and n is 1;

(hereinafter referred to as Metallocene I, which process comprises:

a) mixing (i) liquid aromatic hydrocarbon, or a mixture of a major proportion by weight of liquid aromatic hydrocarbon and a minor proportion of liquid ether with (ii) a crude impure pasty or non-wet reaction mixture containing at least 50% by weight of Metallocene I in whatever form or forms Metallocene I exists in such reaction mixture, to form an anhydrous or substantially anhydrous first mixture;

b) mixing (i) a solution of an organolithium compound in an anhydrous ether solvent or paraffinic hydrocarbon solvent or a mixture thereof in whatever form or forms the organolithium compound exists in such solution, with (ii) the first mixture to form a second mixture, and agitating the second mixture for a period long enough for lithium halide solids to be formed by reaction in the second mixture;

c) separating the solids from the mixture from b), or vice versa, and recovering the resultant liquid portion which consists essentially of a solution of Metallocene II in whatever form or forms Metallocene II exists while in said solution;

d) replacing all or substantially all of the original solvent of the solution from c) with a liquid paraffinic hydrocarbon diluent to form a slurry which consists essentially of Metallocene II product solids in a liquid substantially paraffinic hydrocarbon diluent; and e) recovering said product solids.

40. A process according to claim 39 wherein Metallocene I is 1,1'-dimethylsilylbisindenylhafnium dichloride.

41. A process according to claim 39 wherein Metallocene I is rac-1,1'-dimethylsilylbisindenylhafnium dichloride; wherein (i) of a) is predominately toluene; and wherein the solution of organolithium compound is a solution of methyllithium employed in sufficient quantity to result in replacement of the two chlorine atoms of 1,1'-dimethylsilylbisindenylhafnium dichloride by two methyl groups.

* * * * *